(12) United States Patent
Heinicke

(10) Patent No.: US 7,744,924 B2
(45) Date of Patent: Jun. 29, 2010

(54) VENLAFAXINE FORMULATIONS AND METHODS OF PREPARING THE SAME

(75) Inventor: Grant Heinicke, Rockaway, NJ (US)

(73) Assignee: Actavis Group HF (IS)

( * ) Notice: Subject to any disclaimer, the term of this patent is extended or adjusted under 35 U.S.C. 154(b) by 268 days.

(21) Appl. No.: 11/675,831

(22) Filed: Feb. 16, 2007

(65) Prior Publication Data

US 2007/0134329 A1    Jun. 14, 2007

Related U.S. Application Data

(63) Continuation of application No. 11/024,323, filed on Dec. 28, 2004, now abandoned.

(60) Provisional application No. 60/533,123, filed on Dec. 30, 2003.

(51) Int. Cl.
*A61K 9/16* (2006.01)
(52) U.S. Cl. .................................. 424/490; 424/489
(58) Field of Classification Search ..................... None
See application file for complete search history.

(56) References Cited

U.S. PATENT DOCUMENTS

| | | | |
|---|---|---|---|
| 4,535,186 | A | 8/1985 | Husbands et al. |
| 4,582,705 | A | 4/1986 | Primes et al. |
| 5,026,560 | A | 6/1991 | Makino et al. |
| 5,792,471 | A | 8/1998 | Curatolo |
| 5,912,013 | A | 6/1999 | Rudnic et al. |
| 6,274,171 | B1 | 8/2001 | Sherman et al. |
| 6,310,101 | B1 | 10/2001 | Rudolph et al. |
| 6,403,120 | B1 | 6/2002 | Sherman et al. |
| 6,500,454 | B1 | 12/2002 | Percel et al. |
| 6,572,890 | B2 * | 6/2003 | Faour et al. .................. 424/473 |
| 6,723,348 | B2 * | 4/2004 | Faham et al. ................. 424/490 |
| 6,863,901 | B2 | 3/2005 | Hirsh et al. |
| 2003/0190352 | A1 | 10/2003 | Escoi et al. |

FOREIGN PATENT DOCUMENTS

GB    2 304 727    3/1997

OTHER PUBLICATIONS

A. Kramer, S. Turk, F. Vrecer, International Journal of Pharmaceutics 256 (2003) 43-52, "Statistical Optimisation Diclofenac Sustained Release Pellets Coated with Polymethacrylic Films".
Murali K. Vuppala, Dilip M. Parikh and Hitesh R. Bhagat, Drug Development and Industrial Pharmacy, 23(7), 687-694 (1997) Research Paper, "Application of Powder-Layering Technology and Film Coating for Manufacture of Sustained-release Pellets Using a Rotary Fluid Bed Processor".
Nantharat Pearnchob, Roland Bodmeier, European Journal of Pharmaceutics and Biopharmaceutics 56 (2003) 363-369, "Dry Polymer Powder Coating and Comparison with Conventional Liquid-Based Coatings for Eudragit RS, Ethylcellulose and Shellac".
Angela Y. Lin, Nouman A. Muhammad, David Pope and Larry L. Augsburger, Pharmaceutical Development and Technology, vol. 8, No. 3, pp. 277-287, 2003, "A Study of the Effects of Curing and Storage Conditions on Controlled Release Diphenhydramine HC1 Pellets Coated with Eudragit NE30D".
Nuttanan Sinchaipanid, Padungkwan Chitropas and Ampol Mitrevej, Pharmaceutical Development and Technology vol. 9, No. 2, pp. 163-170, 2004, Research Article, "Influences of Layering on Theophylline Pellet Characteristics".
Martin Wesseling, Roland Bodmeier, European Journal of Pharmaceutics and Biopharmaceutics 47 (1999) 33-38, Research Paper, "Drug Release From Beads Coated With an Aqueous Colloidal Ethylcellulose Dispersion, Aquacoat, or an Organic Ethylcellulose Solution".
Isaac Ghebre-Sellassie and Axel Knoch, "Pelletization Techniques", Encyclopedia of Pharmaceutical Technology, Copyright 2002 pp. 2067-2080.
Shun Li, Kenneth M. Feld, and Chana R. Kowarski, "The Effect of Polymer Coating Systems on the Preparation, Tableting, and Dissolution Properties of Sustained Release Drug Pellets", in Drug Dev. and Indus. Pharm., 23(7), pp. 623-627 (1997).
Non Pareil Seeds (NEU Pellets) as per DuPharm, pp. 1-4, Oct. 14, 2003.
Principles of Polymerization-Third Edition; George Odian, Ed.; John Wiley & Sons, Inc., New York; pp. 20-23; (1991).
Dispensing of Medication—Eighth Edition; John E. Hoover, Ed.; Mack Publishing Company; "Pharmaceutical Factors"; pp. 61-63; (1976).
"Polyethylene Glycol" in Handbook of Pharmaceutical Excipients; Rowe and Sheskey eds.; Pharmaceutical Press; Fourth Edition; pp. 454-459; (2003).
"Polyethylene Oxide" in Handbook of Pharmaceutical Excipients; Rowe and Sheskey eds.; Pharmaceutical Press; Fourth Edition; pp. 460-461; (2003).
Cai, et al.; "Analysis of Interfacial Phenomena of Aqueous Solutions of Polyethylene Oxide and Polyethylene Glycol Flowing in Hydrophilic and Hydrophobic Capillary Viscometers"; Journal of Colloid and Interface Science; 276; pp. 174-181; (2004) Abstract only, 1 page.

* cited by examiner

*Primary Examiner*—Eric E. Silverman
(74) *Attorney, Agent, or Firm*—Cantor Colburn LLP

(57) ABSTRACT

A method of forming a multi-particulate dosage form using rotary granulation is described in which polyethylene oxide is employed as s binder in a rotary granulation process. A multi-particulate oral dosage form comprises a plurality of pellets, the pellets comprising a core having disposed thereon a core composition layer. The core composition layer comprises venlafaxine and a binder, wherein the binder comprises a polyethylene oxide. In other embodiments, the binder comprises a 1:2:1 bis (butyl methacrylate-co-(2-dimethylaminoethyl)methacrylate-co-methyl methacrylate.

17 Claims, No Drawings

VENLAFAXINE FORMULATIONS AND METHODS OF PREPARING THE SAME

CROSS-REFERENCE TO RELATED APPLICATIONS

The present application is a continuation application of U.S. patent application Ser. No. 11/024,323, filed Dec. 28, 2004 now abandoned, which claims priority to Provisional U.S. Patent Application No. 60/533,123 filed Dec. 30, 2003, which are both incorporated by reference in their entirety.

BACKGROUND

Pharmaceutical dosage forms can be in the form of single-unit dosage forms such as tablets, or multi-particulate dosage forms such as pellets. Pellets can be flowable, substantially spherical particulates or rods, for example. Pellets can have a uniform composition or can be in the form of a coated particle such as an inert core having a coating comprising an active pharmaceutical ingredient (API) and optionally excipients. Coating of the cores with the API can be followed by coating of the particles with an extended-release polymer. Optionally, the API-coated particles can be incorporated into an extended release matrix composition. Advantages of dosage forms based on pellets include variable dosage strength without formulation changes, ease of combining incompatible agents, and application of extended-release technology.

There are several manufacturing techniques that can be employed in the formation of pellet dosage forms. Extended-release oral dosage forms of APIs may be prepared using a Wurster process to coat a solution of the API onto inert spheroid particles. This process is characterized by the location of a spray nozzle at the bottom of a fluidized bed of solid particles. The particles are suspended in a fluidizing air stream that is designed to induce a cyclic flow of the particles past the spray nozzle. The nozzle sprays an atomized flow of coating solution, suspension, or other coating vehicle. The Wurster process, while effective, can be time-consuming and can add to manufacturing costs.

A less time-consuming method used to coat APIs is a rotor-granulator process in which centrifugal force, fluidization air velocity, and gravitational force all contribute to the efficiency of the process. In one typical rotor-granulator process, an API powder is deposited on an inert core in the presence of a binder solution. In another typical rotor granulation process, a suspension of the API in a suspending agent is employed. The suspended or powder particles of the API can act to control the size of the atomized droplets. The suspended or powder API particles thus effectively act as a dusting powder to reduce agglomeration that can compete with API layering. In the absence of API particles, e.g., in the presence of an API either wholly soluble or soluble to an appreciable extent in the binder solution, rotor-granulation is usually not performed due to stickiness, slow application rates, and/or formation of a rough surface texture on the particles.

In view of the foregoing problems, the remains a need for improved multi-particulate dosage forms and methods of making the dosage forms.

SUMMARY

A method of making a multi-particulate oral dosage form comprises mixing an active pharmaceutical ingredient, a binder comprising polyethylene oxide, and a dispersing agent to form a coating mixture; and atomizing the coating mixture in the presence of a plurality of cores in a fluidized bed with a rotor-disk granulator to produce a plurality of pellets, the pellets comprising the core having disposed thereon a core composition layer comprising the active pharmaceutical ingredient and the binder.

A multi-particulate oral dosage form comprise a plurality of pellets, the pellets comprising a core having disposed thereon a core composition layer, the core composition layer comprising an active pharmaceutical ingredient and a binder, wherein the binder comprises polyethylene oxide, wherein a ratio of polyethylene oxide to active pharmaceutical ingredient is about 1:30 to about 1:5.

A multi-particulate oral dosage form, comprises a plurality of pellets, the pellets comprising a core having disposed thereon a core composition layer, the core composition layer comprising an active pharmaceutical ingredient and a binder, wherein the binder comprises a 1:2:1 (butyl methacrylate-co-(2-dimethylaminoethyl)methacrylate-co-methyl methacrylate).

DETAILED DESCRIPTION

By "oral dosage form" is meant to include a unit dosage form prescribed or intended for oral administration. An oral dosage form may or may not comprise a plurality of subunits such as, for example, microcapsules or microtablets, packaged for administration in a single dose.

By "subunit" is meant to include a composition, mixture, particle, etc., that can provide an oral dosage form alone or when combined with other subunits. By "part of the same subunit" is meant to refer to a subunit comprising certain ingredients.

By "releasable form" is meant to include immediate-release, controlled-release, and sustained-release forms. Certain release forms can be characterized by their dissolution profile. By "instant-release" is meant a dosage form designed to ensure rapid dissolution of the API by modifying the normal crystal form of the API to obtain a more rapid dissolution. By "immediate-release", it is meant a conventional or non-modified release in which greater then or equal to about 75% of the API is released within two hours of administration, specifically within one hour of administration. "Sustained-release" or "extended-release" include the release of the API at such a rate that blood (e.g., plasma) levels are maintained within a therapeutic range for an extended period of time so that the dosage frequency can be reduced. The term steady-state means that a plasma level for a given API has been achieved and which is maintained with subsequent doses of the API at a level which is at or above the minimum effective therapeutic level and is below the minimum toxic plasma level for a given API.

By "water-soluble" API is meant an API that is at least slightly water-soluble (for example, about 1 to about 10 mg/ml at 25° C.). In some embodiments, APIs are moderately water-soluble (for example, less than about 100 mg/ml at 25° C.), or highly water-soluble (for example, greater than about 100 mg/ml at 25° C.). By "water-insoluble" or "poorly soluble" API, it is meant an API having a water solubility of less than 1 mg/ml, and in some cases even less than 0.1 mg/ml.

A multi-particulate dosage form comprises a plurality of pellets comprising a core having disposed thereon a core composition layer comprising a binder and an API. In one embodiment, the core composition layer is disposed directly on the surface of the core. Exemplary cores include inert spheroids, Nonpareils, sugar spheroids, Cellets®, Celphere®, microcrystalline cellulose spheres, spheres made of microcrystalline cellulose and one or more sugars, such as lactose, and combinations comprising one or more of the foregoing sugars. In one embodiment, the core is a sugar sphere. The size of cores may be, for example, about 250 μm to about 1,400 μm. Commercially available sugar spheres are in U.S. standard sieve size ranges of 14-16, 16-18, 18-20, 20-25, 25-30, 30-35, 40-60, for example. The cores comprise about 10 wt % to about 98 wt %, specifically about 20 wt % to about 90 wt %, and more specifically about 30 wt % to about 60 wt %, of the total weight of the core plus the core composition layer.

It has been established that an API can be efficiently loaded onto a substrate, such as a spheroid, by using an API-binder mixture, wherein the solubility of the API has a profound effect on the processing and yield of the final composition. See, Li et al., "The Effect of Polymer Coating Systems on the Preparation, Tableting, and Dissolution Properties of Sustained Release Drug Pellets," in *Drug Dev. and Indus. Pharm.*, 23(7), p. 623-627 (1997). The term mixture is meant to include both solutions and suspensions. A suitable binder would adhere particles of the selected composition to a core, but would not create such adhesive effects wherein particles of the selected composition adhere to one another. Suitable binders, heretofore typically unused in polymeric systems, include Eudragit® E PO, polyethylene oxide, and combinations comprising one or more of the foregoing binders. For the disclosed novel binders, the ratio of binder to API is about 1:30 to about 1:5.

In an embodiment wherein the binder comprises polyethylene oxide, the polyethylene oxide has the formula —(O—$CH_2$—$CH_2$)$_n$—, wherein n represents the average number of oxyethylene groups, and n is about 2,000 to about 100,000. The polyethylene oxide can have an average molecular weight of about 100,000 to about 6,000,000, such as an average molecular weight of about 300,000 or about 200,000. Alternatively, the polyethylene oxide can have an average molecular weight of about 5,000,000 to about 6,000,000. The polyethylene oxide can have a viscosity of less than or equal to about 200 centipoises (cps) as measured in a 5% aqueous solution, a viscosity greater than or equal to about 6,200 cps as measured in a 1% aqueous solution, a viscosity of about 65 cps to about 115 cps for a 5% aqueous solution as measured at 25° C. on a Brookfield RVT, No. 1 spindle at 50 rpm, or a viscosity of about 7,200 cps to about 10,000 cps for a 1% aqueous solution as measured at 25° C. on a Brookfield RVF, No. 2 spindle at 2 rpm. In certain embodiments, the polyethylene oxide may comprise polyethylene oxide N80, polyethylene oxide N10, and combinations comprising one or more of the foregoing polyethylene oxides. Polyethylene oxide N80 and N10 are commercially available from Dow.

Eudragit® E PO is 1:2:1 (butyl methacrylate-co-(2-dimethylaminoethyl)methacrylate-co-methyl methacrylate), having an average molecular weight of about 150,000. Eudragit® E PO is commercially available from Rohm Pharma Polymers.

The binder comprises about 0.1 wt % to about 20 wt %, specifically about 0.2 wt % to about 10 wt %, and more specifically about 3 wt % to about 8 wt %, of the total weight of the core and the core composition layer.

The core composition layer comprises an API such as venlafaxine or propranolol, suitably in the form of a pharmaceutically acceptable salt. In one embodiment, the API is a water-soluble API. In some embodiments, the API is soluble in the dispersing agent employed in a rotary granulation process. Other suitable APIs include antacids, anti-inflammatory substances, coronary vasodilators, cerebral vasodilators, peripheral vasodilators, anti-infectives, psychotropics, antimanics, stimulants, anti-histamines, laxatives, decongestants, vitamins, gastro-intestinal sedatives, antidiarrheal preparations, anti-anginal drugs, vasodilators, antiarrythmics, anti-hypertensive drugs, vasoconstrictors drugs useful to treat migraines, anticoagulants and antithrombotic drugs, anagesics, anti-pyretics, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs and other drugs or substances acting locally in the mouth, such as topical anagetics, local anaesthetics, etc.

Additional suitable APIs include gastrointestinal sedatives such as metoclopramide and propantheline bromide; antacids such as aluminium, trisilicate, aluminium, hydroxide and cimetidine; anti-inflammatory drugs such as phenylbutazone, indomethacin, naproxen, ibuprofen, flurbiprofen, diclofenac, dexamethasone, predinisone and prednisolone; coronary vasodilator drugs such as glyceryl trinitrate, isosorbide dinitrate and pentaerythritil tetranitrate; peripheral and cerebral vasodilators such as soloctidilum, vincamine, naftidorofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotilline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfoxuccinate; nutritional supplements such as ascorbic acid, alpha tocopherol, thiamine and pyridoxine; antispasmodic drugs such as dicyclomine and diphenoxylate; drugs affecting the rhythm of the heart, such as verapamil, nifedipine, diltiazem, procainamide, disopyramide, bretylium toxylate, quinidine sulfate and quinidine gluconate; drugs used in the treatment of hypertension such as propranolol hydrochloride, guanethidine mono-sulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; anagesic drugs such as acetylsalicyclic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefanamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland disfunction such as triodothyronine, thyroxine and propylthiouracil; diuretic drugs such as furosemide, chlorthalidone, hydrochlorthiazide, spironolactone and trimterene; the uterine relaxant drug ritodrine; appetite suppressants such as fenfluramine hydrochloride, phentermine and diethylproprion hydrochloride; antiasthmatic and bronchodilator drugs such as aminophyline, theophyline, salbutamol, orciprenaline sulphate and terbutaline sulphate;

expectorant drugs such as fuaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; antinauseant drugs such as promethazine theoclate; haemopoietic drugs such as ferrous sulphate, folic acid and calcium gluconate; uricosuric drugs such as sulphinpyrazone, allopurinol and probenecid; drug useful for treating Crohn's disease, e.g., 5-amino salicyclic acid, and the like.

Suitable APIs can also include vitamins such as vitamin A, vitamin D, vitamin B (d-a-tocopherol acetate, etc.), vitamin B, (dibenzoylthiamin, fursultiamine hydrochloride, etc.), vitamin B2 (riboflavin butyrate, etc.), vitamin B6 (pyridoxine hydrochloride, etc.), vitamin C (ascorbic acid, sodium L-ascorbate, etc.), vitamin B12 (hydroxocobalamin acetate, etc.); minerals such as calcium, magnesium, and iron.

In one embodiment, the API is present in the dosage form as a pharmaceutical salt. "Pharmaceutically acceptable salts" includes derivatives of the API, wherein the API is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the propranolol formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; and combinations comprising one or more of the foregoing salts.

The API comprises about 2 wt % to about 85 wt %, more specifically about 10 wt % to about 70 wt %, of the total weight of the core and the core composition layer.

The core composition layer optionally comprises a plasticizer to increase the flexibility of the binder. The added flexibility can allow the binder and drug to adhere more efficiently and uniformly to the core. The plasticizer can be water-soluble or water-insoluble. Exemplary water-soluble plasticizers include triethyl citrate, triacetin, polyethylene glycol, propylene glycol, sorbitol, glycerin, and combinations comprising one or more of the foregoing plasticizers. Exemplary water-insoluble plasticizers include dibutyl sebacate, diethyl phthalate, dibutyl phthalate, tributyl citrate, acetyl tributyl citrate, castor oil, mineral oil, glyceryl monostearate, and combinations comprising one or more of the foregoing plasticizers. In one embodiment, the binder comprises polyethylene oxide and no plasticizer is employed. In another embodiments, the binder comprises Eudragit® E PO and the plasticizer comprises dibutyl sebacate. The plasticizer comprises from about 0 wt % to about 4.5 wt %, specifically about 0.0005 wt % to about 4.5 wt %, and more specifically about 0.001 wt % to about 3 wt %, of the total weight of the core and the core composition layer.

When the core composition layer comprises a plasticizer, the weight of the plasticizer and the binder are considered to be a single entity when determining the ratio of the binder to the API, i.e., the plasticizer is considered to be a part of the binder. For example, the ratio of binder plus plasticizer to API is about 1:30 to about 1:5.

The method comprises combining an API, a binder, optional plasticizer and a dispersing agent to provide a coating mixture. The binder is present in the coating mixture in an amount of about 0.2 wt % to about 20 wt %, of the total weight of the coating mixture. When Eudragit® E PO is present, it is present in an amount of about 1 wt % to about 20 wt %, more specifically about 6 wt % to about 15 wt %, of the total weight of the coating mixture. When polyethylene oxide is present, it is present in an amount of about 0.2 wt % to about 12 wt %, more specifically about 0.5 wt % to about 8 wt %, of the total weight of the coating mixture.

The coating mixture also comprises a dispersing agent. In one embodiment, the binder is soluble in the dispersing agent to allow for easier processing and spraying of the drug onto spheroids. In certain embodiments, the API is soluble in the dispersing agent. Examples of suitable dispersing agents include water, alcohol, isopropyl alcohol, acetone, alcohol USP (95% ethanol, 5% water), SDA-3A alcohol (denatured alcohol with methanol as a denaturant), and combinations comprising one or more of the foregoing dispersing agents. In the final core composition layer, the content of dispersing agent is negligible, if not altogether absent, due to its removal during processing. In one embodiment, when the binder comprises Eudragit® E PO, the dispersing agent comprises an alcohol. In another embodiment, when the binder comprises polyethylene oxide, the dispersing agent comprises a mixture of water and an alcohol, in a water:alcohol ratio of 15:85 to 95:5, specifically 20:80 to 40:60. In one embodiment, the alcohol comprises ethanol. The dispersing agent comprises the balance of the coating mixture.

The API-binder coating mixture may be deposited on the core using a rotary granulation process. The API-binder coating mixture is atomized onto a fluidized bed of cores located in the rotor granulator. Because of the difference in size between the cores and the atomized API-binder mixture, the API sticks to the cores and the binder retains the API on the cores. In the fluidized bed, a rotor-disk granulator makes the cores move with fluid-like motion. As the cores move within the fluidized bed, they are sprayed with the API-binder mixture until the desired quantity of API is deposited upon the cores. Coating of the API and binder may optionally be followed by a drying step.

In the case of Eudragit® E PO, it has been found that Eudragit® E PO can be employed as a binder for formulations processed in a rotary granulation process. In the case of polyethylene oxide, it has been found that the use of polyethylene oxide as a binder allows for unexpectedly efficient processing in a rotary granulation process. For example, polyvinylpyrrolidone (PVP), a binder typically employed in rotary granulation processes, has slow processing times in rotary granulation processing, particularly when the API has high solubility in the dispersing agent used for processing, such as venalfaxine in a water/ethanol solution. Substitution of polyethylene oxide for PVP reduced processing times by a factor of greater than or equal to about 2. In another embodiment, the process recovery was unexpectedly high. For example, the yield of the recovered product was about 100% without observable dust or agglomeration.

In a rotary granulation process, typically the API is suspended and not dissolved in the dispersing agent. A particular advantage of polyethylene oxide as a rotary granulation binder may be apparent when the quantity of API and the identity of the dispersing agent employed are such that greater than or equal to about 30%, 40%, 50%, 60%, 70%, 80%, 90%, 95%, 99%, or 100% of the API is dissolved in the dispersing agent. The amount of API dissolved in the dispersing agent is dependent upon the volume of the dispersing agent employed relative to the amount of API. In many cases, it is desirable to decrease the volume of the solvent to maintain the API in suspension. While the volume of the dispersing agent can be decreased to compensate for the solubility of the API, it can be disadvantageous to greatly decrease the volume of the dispersing agent due to problems of increased viscosity and difficulties in atomization. Alternatively, increased quantities of solvent can facilitate atomization, but can dissolve more of the API leading to processing problems such as stickiness. In one embodiment, a particular advantage as noted in the reduction in the processing rate with polyethylene oxide is observed when greater than or equal to about 30%, specifically about 50% to about 100% of the API is dissolved in the dispersing agent. Polyethylene oxide can be advantageous compared to other binders such as PVP when a particular dispersing agent is employed at a particular volume.

The temperature, pressure, spraying rate, and plate speed may be adjusted to prevent agglomeration of the API, and to allow for efficient API-substrate interaction. At high temperatures, the composition of an API such as venlafaxine, binder, dispersing agent and optionally a plasticizer, can evaporate before adhering to the spheroids. Also, at lower temperatures, the spheroids as well as the API can agglomerate leading to the production of large agglomerates. The pressure in the spraying nozzle should be sufficient to atomize the API composition, without making the atomized particles too small to adhere to the substrate. Preferably, the pressure level retains the size of the atomized particles to act as their own anti-dusting agents, wherein agglomeration is limited. The spray rate can be optimized to prevent the API composition from being lost during the processing, or excessive wetting.

The processing conditions are dependent upon rotary granulator size and type, for example, and thus the following conditions are exemplary and non-limiting. In one embodiment in which Eudragit® E PO is used as a binder, the inlet air temperature in the fluidized bed is about 35° C. to about 45° C., more specifically about 38° C. to about 42° C.; the dew point is about −5° C. to about 15° C., specifically about −4° C. to about −1° C.; the outlet air temperature is about 16° C. to about 20° C., specifically about 17° C. to about 19° C.; the product temperature is about 16° C. to about 20° C.; the atomizing air pressure is about 1 to 2 bar, specifically 1.5 bar; and the spraying rate is about 20 to 45 grams/minute, specifically about 37 to about 43 grams/minute.

In another embodiment, in which polyethylene oxide is used as a binder, the inlet air temperature in the fluidized bed is about 45° C. to about 55° C., specifically about 48° C. to about 52° C.; the dew point is about −3° C. to about 1° C.; the outlet air temperature is about 32° C. to about 45° C.; the product temperature is about 33° C. to about 43° C.; the atomizing air pressure is about 2.5 bar to about 3.5 bar, specifically 3 bar; and the spraying rate is about 6 to about 9 grams/minute. The plate speed may be about 290 to about 320 rpm.

Optionally, following the application of the core coating composition, the pellets may be coated with additional coatings such as a controlled-release coating or a seal coating. Controlled-release coatings can include, for example, film-forming agents, pore-forming agents, plasticizers, anti-tacking agents, and combinations comprising one or more of the foregoing agents. Exemplary film-forming agents include ethyl cellulose, Eudragit® NE 30D, cellulose acetate, cellulose acetate butyrate, Eudragit® RS, Eudragit® RL, and combinations comprising one or more of the foregoing film-forming agents. Exemplary pore-forming agents include pH-independent and pH-dependent agents. Exemplary pH-independent pore-forming agents include polyvinylpyrrolidone, hydroxy propyl cellulose, hydroxy propylmethyl cellulose, hydroxyethyl cellulose, polyethylene glycol, methyl cellulose, and combinations comprising one or more of the foregoing pH-independent pore-forming agents. Exemplary pH-dependent pore forming agents include hydroxy propylmethyl cellulose phthalate, Eudragit® L 100-55, Eudragit® L 30D, Eudragit® S, Eudragit® FS 30D, polyvinyl acetate phthalate, shellac, cellulose acetate trimellitate, cellulose acetate phthalate, and combinations comprising one or more of the foregoing pH-dependent pore-forming agents. Exemplary plasticizers include triethyl citrate, tributyl citrate, acetyl tributyl citrate, acetyl triethyl citrate, triacetin, castor oil glycerol, dibutyl sebacate, diethyl phthalate, and combinations comprising one or more of the foregoing plasticizers. Exemplary anti-tacking agents include talc, colloidal silicon dioxide, glyceryl monostearate, and combinations comprising one or more of the foregoing anti-tacking agents.

The controlled-release coating composition can be applied to the core using a coating technique used in the pharmaceutical industry, such as fluid bed coating. Once applied and dried, the controlled-release polymers in the controlled-release coating may comprise about 2 wt % to about 30 wt % of the total weight of the coated cores, or about 7 wt % to about 20 wt % of the total weight of the coated cores. In this context, coated core means the pellet comprising the API plus any additional coatings.

The controlled-release coating may be dried before applying an optional second coating. A color imparting agent may be added to the controlled-release coating composition or a rapidly dissolving seal coat containing color may be coated over the controlled release coating layer provided that the seal coat is compatible with and does not affect the dissolution of the controlled-release coating layer.

The multi-particulate dosage form of the API is optionally encapsulated in hard gelatin to provide a desired quantity of API in an oral dosage form. Immediate-release API cores can be combined with extended-release coated cores and together encapsulated in hard gelatin. Alternatively, the multi-particulate dosage form may be made into tablets, for example, by first adding about 25 wt % to about 40 wt % of a solid pharmaceutically acceptable tablet excipient which will form a compressible mixture with the coated cores and which may be formed into a tablet without crushing the coated cores, and optionally an effective amount of a tablet disintegrating agent and a lubricant. The solid pharmaceutically acceptable tablet excipient may comprise, for example, lactose, dextrose, mannitol, calcium phosphate, microcrystalline cellulose, kaolin, powdered sucrose, and combinations comprising one or more of the foregoing excipients. The tablet disintegrant may comprise crospovidone, croscarmellose sodium, dry starch, sodium starch glycolate, and the like, and combinations comprising one or more of the foregoing disintegrants. Suitable lubricants include, for example, calcium stearate, glycerol behenate, magnesium stearate, mineral oil, polyethylene glycol, sodium stearyl fumarate, stearic acid, talc, vegetable oil, zinc stearate, and combinations comprising one or more of the foregoing lubricants.

EXAMPLES

The following examples further illustrate the invention but, of course, should not be construed as in any way limiting its scope. In particular, the processing conditions are merely exemplary and can be readily varied by one of ordinary skill in the art.

Example 1

This example illustrates the production of an exemplary API oral dosage formulation.

82 grams of Eudragit® EPO were dissolved in 1,020 grams of alcohol to provide a mixture. Then, 20 grams of dibutyl sebacate were added to the mixture and stirred for 30 minutes. To the resulting mixture, 1,020 grams of venlafaxine HCl were added and stirred to form a suspension of the API. Sugar spheroids, having a total mass of 1000 grams, were charged into a Glatt GPCC-3 rotor-disk fitted with a Schlick 970 spray gun. The suspension of API and plasticized binder (coating mixture). The suspension was applied to the sugar spheroids in a rotary granulator under the processing conditions given in table 1:

TABLE 1

| Parameter | Set Point |
| --- | --- |
| Inlet Air temperature | 40° C. |
| Process air volume | 80 cfm |
| Plate speed | 300 rpm |
| Slurry application rate | 80 g/min average over batch |
| Atomizing air pressure | 1 bar |
| Product temperature | 15-20° C. |

After a desired concentration of venlafaxine was applied to the spheroids, product was recovered having a size between 710 and 1,400 μm. The final composition of the product is given in table 2.

TABLE 2

| Material | Amount (g) | wt % Composition |
| --- | --- | --- |
| Venlafaxine HCl | 1,020 | 48.0 |
| Spheroids (# 20-25) | 1,000 | 47.1 |
| Eudragit ® E PO | 82 | 3.9 |
| Dibutyl sebacate | 20 | 1.0 |
| Alcohol | 1,020 | Not present in final product |

Example 2

This example illustrates the production of another exemplary API oral dosage formulation.

102 grams of polyethylene oxide were dissolved in an alcohol/water mixture to provide a mixture. To the mixture, 1,020 grams of Venlafaxine HCl were added and stirred to form a clear solution. Sugar spheroids, of size #20-25 and having a total mass of 1,000 grams, were charged into a Glatt GPCG-3 rotor-disk fitted with a Schlick 970 spray gun. The API/binder coating mixture was applied to the sugar spheroids in a rotary granulator under the processing conditions given in table 3:

TABLE 3

| Parameter | Set Point |
| --- | --- |
| Inlet Air temperature | 50° C. |
| Process air volume | 80 cfm |
| Plate speed | 311 rpm |
| Slurry application rate | 30 g/min average over batch |
| Atomizing air pressure | 3 bar |
| Product temperature | 33-43° C. |

After a desired concentration of venlafaxine was applied to the spheroids, product was recovered having a size between 710 μm and 1,400 μm. The final composition of the product is given in table 4.

TABLE 4

| Material | Amount (g) | wt % Composition |
| --- | --- | --- |
| Venlafaxine HCl | 1,020 | 48.0 |
| Spheroids (# 20-25) | 1,000 | 47.1 |
| Polyox ™Sentry WSR N80 | 102 | 4.9 |
| Alcohol | 2,040 | Not present in final product |
| Water USP | 640 | Not present in final product |

Example 3

This example describes preparation of another extended-release oral dosage formulation.

102 grams PEO was dissolved in 2,680 grams of an alcohol/water mixture. 1,020 grams of Venlafaxine HCl was added to the binder mixture with stirring to form a clear solution. 100 grams of sugar spheres were charged into a Glatt GPCG-3 rotor fitted with a Schlick 970 spray gun. The API/binder solution was applied to the sugar spheres in a rotary granulator under the process conditions given in Table 5:

TABLE 5

| Parameter | Set Point |
| --- | --- |
| Inlet Air temperature | 50° C. |
| Process air volume | 80 cfm |
| Plate speed | 307 rpm |
| Slurry application rate | 20 g/min average over batch |
| Atomizing air pressure | 3 bar |
| Product temperature | 37-45° C. |

Processing was fast and efficient with a processing time of 190 minutes. The recovered product had a size of 710-1400 μm with no observable dust or agglomeration. The final composition of the product is given in table 6.

TABLE 6

| Material | Amount (g) | wt % Composition |
| --- | --- | --- |
| Venlafaxine HCl | 1,020 | 48.0 |
| Sugar Spheres | 1,000 | 47.1 |

TABLE 6-continued

| Material | Amount (g) | wt % Composition |
|---|---|---|
| Polyox ™Sentry WSR N10 | 102 | 4.9 |
| Alcohol | 2,040 | Not present in final product |
| Water USP | 640 | Not present in final product |

Comparative Example 1

For comparison, venalfaxine was coated onto sugar spheres using polyvinylpyrolidone as a binder and ethanol as a dispersing agent. The venlafaxine was applied at 50 wt %. As is typical for a solution, the sugar spheres were coated using a Wurster process. The coating process took 7 hours.

Novel binder systems for the formation of API-binder coated cores in multi-particulate dosage forms have been described. The novel binders are particularly advantageous for use in a rotary granulator process wherein improved processing times may be observed. In particular, polyethylene oxide can reduce processing times by a factor of two or more compared to conventional binders such as PVP. Another advantage is that APIs can be applied to a core in the form of a solution rather than a suspension in a rotary granulation process. Yet another advantage is that product recoveries approaching 100% can be achieved.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A multi-particulate oral dosage form, comprising a plurality of pellets, the pellets comprising a core having disposed thereon a core composition layer, the core composition layer comprising an admixture of venlafaxine and a binder, wherein the binder comprises polyethylene oxide, wherein the polyethylene oxide has an average molecular weight of about 100,000 to about 6,000,000, and wherein a ratio of polyethylene oxide to venlafaxine is about 1:30 to about 1:5.

2. The multi-particulate oral dosage form of claim 1, wherein the binder comprises about 0.2 wt % to about 12 wt % of the total weight of the core and the core composition layer.

3. The multi-particulate oral dosage form of claim 1, comprising about 10 wt % to about 98 wt % of the core, about 2 wt % to about 85 wt % of the venlafaxine, and about 0.1 wt % to about 20 wt % of the binder, all based on the total weight of the core and the core composition layer.

4. The multi-particulate oral dosage form of claim 3, comprising about 10 wt % to about 70 wt % of the venlafaxine, based on the total weight of the core and the core composition layer.

5. The multi-particulate oral dosage form of claim 1, further comprising an additional coating layer, wherein the additional coating layer is a controlled-release coating, a seal coating, or a combination of one or more of the foregoing coatings.

6. The multi-particulate dosage form of claim 1, wherein the core is an inert sphere.

7. The multi-particulate dosage form of claim 6, wherein the inert sphere comprises nonpareils, sugar spheroids, microcrystalline cellulose spheres, spheres made of microcrystalline cellulose and one or more sugars, or a combination of one or more of the foregoing cores.

8. The multi-particulate dosage form of claim 1, wherein the inert sphere is a sugar sphere.

9. The multi-particulate dosage form of claim 1, wherein the core composition layer further comprises a plasticizer.

10. A multi-particulate oral dosage form, comprising a plurality of pellets, the pellets comprising an inert sphere core having disposed thereon a core composition layer, the core composition layer comprising an admixture of venlafaxine, a plasticizer, and a binder, wherein the binder comprises a 1:2:1 (butyl methacrylate-co-(2-dimethylaminoethyl)methacrylate-co-methyl methacrylate).

11. The multi-particulate oral dosage form of claim 10, wherein the ratio of binder to venlafaxine in the core composition layer is about 1:30 to about 1:5.

12. The multi-particulate oral dosage form of claim 10, wherein the binder comprises about 0.2 wt % to about 12 wt % of the total weight of the core and the core composition layer.

13. The multi-particulate oral dosage form of claim 10, comprising about 10 wt % to about 98 wt % of the core, about 2 wt % to about 85 wt % of the venlafaxine, and about 0.1 wt % to about 20 wt % of the binder, all based on the total weight of the core and the core composition layer.

14. The multi-particulate oral dosage form of claim 13, comprising about 10 wt % to about 70 wt % of the venlafaxine, based on the total weight of the core and the core composition layer.

15. The multi-particulate oral dosage form of claim 1, further comprising an additional coating layer, wherein the additional coating layer is a controlled-release coating, a seal coating, or a combination of one or more of the foregoing coatings.

16. The multi-particulate dosage form of claim 10, wherein the inert sphere is a sugar sphere.

17. A method of making a multi-particulate oral dosage form, of claim 1 comprising mixing venlafaxine, a binder comprising polyethylene oxide, and a dispersing agent to form a coating mixture, and atomizing the coating mixture in the presence of a plurality of cores in a fluidized bed with a rotor-disk granulator to produce a plurality of pellets, the pellets comprising the core having disposed thereon a core composition layer comprising the venlafaxine and the binder.

* * * * *